United States Patent [19]

Chesne et al.

[11] Patent Number: 4,898,963

[45] Date of Patent: Feb. 6, 1990

[54] PROCESS FOR THE RECOVERY OF ACID ORGANOPHOSPHORUS COMPOUNDS AND/OR ORGANOPHOSPHATE IONS PRESENT IN AN AQUEOUS SOLUTION

[75] Inventors: André Chesne, le Vesinet; Sylvie Chevalier, Paris; Michel Germain, Marcoussis; Dominique Pareau, Verrieres le Buisson, all of France

[73] Assignee: Commissariat a l'Energie Atomique, Paris, France

[21] Appl. No.: 114,622

[22] Filed: Oct. 29, 1987

[30] Foreign Application Priority Data

Oct. 30, 1986 [FR] France ................................ 86 15127

[51] Int. Cl.[4] ................................ C07C 9/08

[52] U.S. Cl. ................................ 558/146

[58] Field of Search ................................ 558/146

[56] References Cited

U.S. PATENT DOCUMENTS 3,150,149 9/1974 Schmitt ................................ 260/429.1

FOREIGN PATENT DOCUMENTS 2132756 11/1972 France .

2359486 2/1978 France .

941791 11/1963 United Kingdom ................................ 558/146

*Primary Examiner*—Anton H. Sutto

*Attorney, Agent, or Firm*—Michael N. Meller

[57] ABSTRACT

The invention relates to the recovery of acid organophosphorus compounds and/or organophosphate ions present in an aqueous solution.

According to the invention, the aqueous solution is contacted with at least one organic amino compound which is not very soluble in water, chosen from among compounds having at least one amine function, the salts of these amino compounds and the quaternary ammonium salts and the complex formed is separated from the aqueous solution by reacting these acid organophosphorus compounds and/or organophosphate ions with the organic amino compound or compounds.

The amino compound can be a trialkylamine, e.g. triisooctyl amine and contacting and separation can be performed in a co-current or counter-current liquid-liquid extraction installation.

10 Claims, No Drawings

PROCESS FOR THE RECOVERY OF ACID ORGANOPHOSPHORUS COMPOUNDS AND/OR ORGANOPHOSPHATE IONS PRESENT IN AN AQUEOUS SOLUTION

DESCRIPTION

The invention relates to a process for the recovery of acid organophosphorus compounds and/or organophosphate ions present in an aqueous solution.

More specifically, it relates to the treatment of aqueous effluents containing such organophosphorus compounds with a view to recovering the latter which are disturbing products for the environment and can in certain cases be reused for the separation of metals by liquid—liquid extraction.

For some years, an increasing use has been made in industry of acid organophosphorus compounds for bringing about the separation of metals by liquid—liquid extraction. These compounds are generally constituted by monoalkylphoshoric or dialkylphosphoric acids, such as di-2-ethylhexylphosporic acid, which have interesting properties for the purification of numerous metals such as nickel, copper, zinc, rare earths, uranium and plutonium.

These acid organophosphorus compounds or their salts with mineral cations are very slightly soluble in water, so that aqueous solutions leaving extraction installations consequently contain small quantities of acid organophosphorus compounds, which are preferably recovered before the disposing of the effluents, on the one hand for preventing pollution of the environment and on the other for recovering said extractants and the recycling thereof into the liquid—liquid extraction installation.

Acid organophosphorus compounds not usable for extraction can also occur in effluents coming from installations for the liquid—liquid extraction of metals. This is e.g. the case with uranium and/or plutonium extraction installations using tributyl phosphate as the extractant, because degration by hydrolysis, photolysis and/or radiolysis of the tributyl phosphate leads to the formation of mono- and di-butylphosphoric acids. The presence of these acids in the organic extraction phase may disturb the extraction process. They are generally extracted from this organic phase by washing in a basic aqueous solution, which leads to the production of basic effluents containing organophosphorus acid salts. In this case, it is also desirable to extract these organophosphorus compounds before disposing of the aqueous effluents. This recovery of acid organophosphorus compounds and/or organophosphate ions causes certain problems, because the pH of the aqueous solutions containing the same can vary within a wide range. Thus, these solutions can result from extractions performed in an acid medium, such as is e.g. the case with dilute sulphuric solutions from which various metals have been extracted. They can also be constituted by basic solutions and this is e.g. the case with the solutions for washing solvents coming from the installations for the treatment of irradiated fuels using tributyl phosphate.

Among the processes making it possible to treat aqueous effluents of this type, a process for the extraction of mono- and di-butylphosphoric acids present in the carbonated basic solutions in known and consists of firstly acidifying the carbonated solution by adding nitric acid in order to bring its acidity to a value of 3–4N and then extract the phosphoric acids by 2-ethyl-1-hexanol, as is described by E. H. Horwitz et al "Actinide Separations", Honolulu, Hawaii, Apr. 3–5, 1979, p. 475, ACS Symposium Series 117.

This method suffers from the disadvantage of only being usable in a restricted acidity range which can cause certain problems, because this acidification can lead to precipitations or to chemical reactions of a disturbing nature in the effluent to be treated.

The present invention relates to a process for the recovery of acid organophosphorus compounds and/or organophosphate ions present in an aqueous solution obviating the aforementioned disadvantage.

The inventive process for the recovery of acid organophosphorus compounds and/or organophosphate ions present in an aqueous solution is characterized in that the aqueous solution is contacted with at least one organic amino compound which is only slightly soluble in water and chosen from among compounds having at least one amine function, the salts of said amino compounds with an acid and quaternary ammonium salts and in that from the aqueous solution is separated the complex formed by reaction of acid organophoshorus compounds and/or organophosphate ions with the organic amino compound or compounds.

According to the invention, the amino compounds used must be only slightly soluble in water, so as not to pollute the aqueous solution with which they are contacted. Generally an amino compound is chosen, whose solubility in water does not exceed approximately 1 mg/l.

For example, the organic amino compound used can be a primary, secondary or tertiary amine or a quaternary ammonium salt. It can also be constituted by a salt obtained by reacting a primary, secondary or tertiary amine with an inorganic acid, such as hydrochloric acid, or an organic acid, such as formic or acetic acid. It is also possible to use an amine partly salified by an acid.

The amines which can be used are preferably alkyl amines, especially trialkyl amines, such as triisooctylamine. However, it is also possible to use cyclic amines, e.g. dibenzylamine and tribenzylamine.

In the process according to the invention, the acid organophosphorus compound AH or the organophosphate ions $A^-$ react with the organic compound having an amine function RN or with its salt $RN^+H \ldots B^-$ in accordance with the following reaction diagrams:

$$AH + RN \rightleftarrows RN^+H \ldots A^-$$

$$A^- + RN^+H \ldots B^- \rightleftarrows RN^+H \ldots A^- + B^-$$

in which RN can represent a primary amine $RNH_2$, a secondary amine RR'NH or a tertiary amine RR'R"N. This gives a complex which can then be separated from the aqueous solution.

In the case where use is made as the organic amino compound of a quaternary ammonium salt of formula $RR'R''R'''N^+ \ldots B^-$, which is symbolized by $R_4N^+ \ldots B^-$, the acid organophosphorus compound AH or the organophosphate ions $A^-$ react with this quaternary ammonium salt in accordance with the following reaction diagrams:

$$AH + R_4N^+ \ldots B^- \rightleftarrows R_4N^+ \ldots A^- + BH$$

$$A^- + R_4N^+ \ldots B^- \rightleftarrows R_4N^+ \ldots A^- + B^-$$

which constitute an anion exchange mechanism. The $B^-$ anions (minerals such as $NO_3^-$, $Cl^-$, etc.) will be displaced by the organophosphate ions $A^-$, thus making it possible to separate the acid organophosphorus compounds or the organophosphate ions from aqueous solutions.

The inventive process can be used for treating very varied aqueous solutions having pH-values extending in a wide range, which can e.g. range from 0.3 to very basic pH-values exceeding 12.5, whilst still retaining a very good effectiveness at these very basic pH-values.

In order to favour the separation of the complex formed, it is possible to use an organic amino compound in a water-immiscible organic phase, so as to extract the complex in the organic phase. In this case, the process can be performed in a solvent extraction installation in which the aqueous solution to be treated is brought into co-current or counter-current contact with the organic phase containing at least one of the aforementioned amino compounds. Generally the organic amino compound is dissolved or diluted in an organic solvent, which can be constituted by an aromatic or paraffinic hydrocarbon, a chloro compound such as $CHCl_3$ or $CCl_4$, an ether, an ester, an alcohol and a ketone, which can be used alone or in mixed form. Preferably, according to the invention, use is made of an organic solvent constituted by a mixture of a hydrocarbon and an alcohol, e.g. a mixture of n-dodecane and 1-octanol.

The extraction apparatuses usable are conventional equipments, such as mixer—settler groups, liquid—liquid extraction columns (pulsed, stirred, lined, etc.) and liquid—liquid chromatography columns. In such apparatuses, the flow-rates of the aqueous solution and the organic solution are chosen in such a way as to obtain the desired contact time between the two solutions. In the same way, the amino compound concentration of the organic solution is chosen as a function of its solubility in the solvent, so as to obtain a good extraction of the acid organophosphorus compounds or organophosphate ions, whilst still having good physicochemical characteristics linked with the hydrodynamics of the systems.

Generally, extraction takes place at ambient temperature, but it is possible to work at higher temperatures, ranging e.g. from 20° to 50° C., or at temperatures below ambient temperature, if this proves to be necessary.

According to a variant of the invention, it is also possible to facilitate the separation of the complex formed during the reaction by contacting the aqueous solution containing the acid organophosphorus compounds or the organophosphate ions with a solid support to which is fixed the organic compound, which may be dissolved or diluted in the aforementioned organic solvents. In this caee, it is possible to use liquid—liquid chromatography methods for realizing the reaction and separation stages.

The process according to the invention is applicable to numerous acid organophosphorus and/or organophosphate compounds. However, it is normally used for recovering acid organophosphorus compounds constituted by mono- or di-alkylphosphoric acids or the corresponding organophosphate ions.

Other characteristics and advantages of the invention can be better gathered from studying the following examples given in a non-limitative manner for illustrating the inventive process.

EXAMPLE 1

Use of a Primary Amine

In this example, aqueous solutions are treated, which contain $4.4\cdot10^{-3}$ mole$\cdot l^{-1}$ of dibutylphosphoric acid (DBP) and 0.1 mole$\cdot l^{-1}$ of $NaNO_3$, having pH-values between 4.5 and 7, by using as the organic phase the product PRIMENE JMT, which is a mixture of primary amines having 18 to 22 carbon atoms in nitrate form at a concentration of 0.38 mole$\cdot l^{-1}$ in a mixture of 1-octanol and n-dodecane containing 18% 1-octanol and 82% n-dodecane. Contacting takes place for 5 minutes at ambient temperature using equal volumes of aqueous solution and organic solution. After the settling of the phases, the DBP concentrations of the aqueous phase and the organic phase are determined. This gives the value of the coefficient of partition D of dibutylphosphoric acid DBP, which is equal to the ratio of the DBP concentration of the organic phase to the DBP concentration of the aqueous phase. Under the aforementioned conditions, the coefficient of partition D of DBP is always above 40.

EXAMPLE 2

Use of a Secondary Amine

In this example, contacting takes place between aqueous solutions containing 0.1 mole$\cdot l^{-1}$ of $NaNO_3$ and $5.3\cdot10^{-3}$ mole$\cdot l^{-1}$ of DBP with pH-values between 3 and 7.1 and an organic phase constituted by Genamine Nitrate CS200 (Hoechst) dissolved in a mixture of 1-octanol and n-dodecane with 18% octanol and 82% dodecane. Genamine is a mixture of secondary amines containing 51% of amine with 12 carbon atoms, 22% of amine with 14 carbon atoms, 11% of amine with 16 carbon atoms and 14% of amine with 18 carbon atoms. Extraction takes place as in example 1, but whilst working at a temperature of 50° C. The coefficients of partition of DBP are always above 50 for these solutions.

EXAMPLE 3

Use of a Quaternary Ammonium Salt

Aqueous solutions having a pH between 2.5 and 12.5 and containing 0.1 mole$\cdot l^{-1}$ of $NaNO_3$ and $4.8\cdot10^{-3}$ mole$\cdot l^{-1}$ of DBP are contacted with an organic phase constituted by tetraheptylammonium chloride at a concentration of 0.4 mole$\cdot .^{-1}$ in a mixture of 18% octanol and 82% n-dodecane. Contacting takes place for 5 minutes at a temperature of 20° C. using equal volumes of the aqueous and organic phases. The coefficient of partition of DBP always exceeds 40.

EXAMPLE 4

Use of a Tertiary Amine

In this example, an aqueous solution containing $5\cdot10^{-3}$ mole$\cdot l^{-1}$ of dibutylphosphoric acid (DBP) and 0.5 mole$\cdot l^{-1}$ of sodium chloride is treated using as the organic phase triisooctylamine diluted to 0.44 mole$\cdot l^{-1}$ in a mixture of n-dodecane and 1-octanol with 16% by volume of the latter.

One volume of the aqueous solution is contacted with one volume of the organic phase for 5 minutes and accompanied by stirring. The phases are then allowed to settle and the dibutylphosphoric acid concentrations of the aqueous and organic phases are determined. This gives the value of the coefficient of partition D of the dibutylphosphoric acid between the aqueous phase and the organic phase and this is equal to the ratio of the DBP concentration of the organic phase to the DBP concentration of the aqueous phase.

Under the conditions described hereinbefore, the coefficient of partition D of dibutylphosphoric acid is 35.

EXAMPLE 5

The same operating procedure as in example 4 is used, but the initial aqueous solution contains 0.5 mole·$l^{-1}$ of sodium nitrate in place of sodium chloride. Under these conditions, the coefficient of partition D of dibutylphosphoric acid is 30.

EXAMPLE 6

The same operating procedure as in example 4 is repeated, but the initial aqueous solution contains 0.5 mole·.$l^{-1}$ of sodium perchlorate instead of sodium chloride. Under these conditions, the coefficient of partition D is 15.

EXAMPLE 17

The same operating procedure as in example 4 is repeated, but the initial aqueous solution contains 0.5 mole·.$l^{-1}$ of sodium sulphate in place of sodium chloride. Under these conditions, the coefficient of partition D of dibutylphosphoric acid is 59.

On the basis of these examples, it can be seen that the use of triisooctylamine makes it possible to purify by more than 93% all the solutions treated in examples 4 to 7, the majority being purified by more than 95%.

EXAMPLE 8

The operating procedure of example 4 is repeated, the aqueous solution being on the occasion a solution containing 0.45 mole·$l^{-1}$ of nitric acid, 5.3 g·$l^{-1}$ of trivalent plutonium, 0.1 mole·$l^{-1}$ of hydrazinium nitrate and $5 \cdot 10^{-3}$ mole·$l^{-1}$ of DBP. An organic phase constituted by 0.44 mole·$l^{-1}$ triisooctylamine is used in a mixture of octanol and n-dodecane containing 16% by volume of octanol. Under these conditions, the coefficient of partition of DBP is equal to 50 and that of plutonium is equal to 0.06.

EXAMPLE 9

In this example, an aqueous solution is treated, which is obtained during the washing of tributylphosphate (TBP) used in a cycle for purifying plutonium and uranium. TBP washing is performed with a carbonic aqueous solution obtained by the partial neutralization of hydrazine base by $CO_2$. The aqueous solution leaving the washing installation contains $4.78 \cdot 10^{-3}$ mole·l.$^{-1}$ of dibutylphosphate and its pH is adjusted to a value of 6.8 by adding nitric acid. It is then treated in accordance with the process of the invention in a counter-current liquid—liquid extraction installation having two stages, using an organic phase having as the solvent a mixture of n-dodecane and 1-octanol with 16% byy volume of 1-octanol, containing 0.32 mole·$l^{-1}$ of triisoctylamine and 0.12 mole·$l^{-1}$ of triisooctyl ammonium salt.

This installation uses an aqueous flow rate/organic flow rate ratio of 0.46 and on leaving the installation an aqueous phase is collected, whose dibutyl phosphate content is $0.08 \cdot 10^{-3}$ mole·$l^{-1}$, which corresponds to a 98.4% purification rate.

It is also pointed out that plutonium IV, which is present in the aqueous phase, is not extracted in the organic phase, the coefficient of partition of plutonium being below $1.2 \cdot 10^{-2}$. In addition, the purified aqueous solution can be recycled for subsequent fissile material recovery treatment.

We claim:

1. Process for the recovery of acid organophosphorus compounds, organophosphate ions and mixtures thereof present in an aqueous solution, comprising contacting the aqueous solution with an organic solution comprising at least one organic amino compound which is not very soluble in water and which is dissolved or diluted in an organic solvent, said organic solvent selected from the group consisting of aromatic and paraffinic hydrocarbons, organochloro compounds, ethers, esters, alcohols, ketones and mixtures thereof, wherein said organic amino compounds have at least one amine function selected from the group consisting of cyclic amines; primary, secondary and tertiary amines; acid salts of these amino compounds, quaternary ammonium salts, and mixtures thereof, and recovering, in the organic solution, the complex formed by the reaction of the acid organophosphorus compounds, organophosphate ions and mixtures thereof with one or more of the organic amino compounds.

2. Process according to claim 1, characterized in that the organic amino compound is a primary, secondary or tertiary amine, or a quaternary ammonium salt.

3. Process according to claim 2, characterized in that the organic amino compound is a trialkylamine.

4. Process according to claim 3, characterized in that the amine is partly or totally salified by an acid.

5. Process according to claim 3, characterized in that the trialkylamine is triisooctylamine.

6. Process according to claim 1, characterized in that the organic solvent is a mixture of a hydrocarbon and an alcohol.

7. Process according to claim 6, characterized in that the organic solvent is a mixture of n-dodecane and 1-octanol.

8. Process according to claim 1, characterized in that the acid organophosphorus compounds are monoalkylphosphoric or dialkylphosphoric acids.

9. Process for the treatment of aqueous effluents containing aci organophosphorus compounds, organophosphate ions and mixtures thereof characterized in that it consists of extracting from these effluents the acid organophosphorus compounds the organophosphate ions by realizing the process according to claim 1.

10. A process according to claim 1 wherein the organochloro compound is $CHCl_3$ or $CCl_4$.

* * * * *